United States Patent
Tanner et al.

(10) Patent No.: US 9,795,552 B2
(45) Date of Patent: *Oct. 24, 2017

(54) SUPERABSORBENT POLYMERS AND SILICONE ELASTOMER FOR USE IN SKIN CARE COMPOSITIONS

(71) Applicant: The Procter & Gamble Company, Cincinnati, OH (US)

(72) Inventors: Paul Robert Tanner, Cincinnati, OH (US); Mridula Manohar, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/828,088

(22) Filed: Aug. 17, 2015

(65) Prior Publication Data
US 2015/0352028 A1 Dec. 10, 2015

Related U.S. Application Data

(63) Continuation of application No. 13/834,083, filed on Mar. 15, 2013, now abandoned.

(60) Provisional application No. 61/612,617, filed on Mar. 19, 2012.

(51) Int. Cl.
| | |
|---|---|
| *A61K 8/81* | (2006.01) |
| *A61K 8/91* | (2006.01) |
| *A61Q 5/12* | (2006.01) |
| *A61K 8/891* | (2006.01) |
| *A61K 8/34* | (2006.01) |
| *A61K 8/894* | (2006.01) |
| *A61K 8/11* | (2006.01) |
| *A61K 8/06* | (2006.01) |
| *A61K 8/67* | (2006.01) |
| *A61K 8/26* | (2006.01) |
| *A61K 8/73* | (2006.01) |
| *A61Q 15/00* | (2006.01) |
| *A61K 8/89* | (2006.01) |
| *A61Q 17/04* | (2006.01) |
| *A61Q 19/00* | (2006.01) |
| *A61K 8/893* | (2006.01) |
| *A61Q 19/02* | (2006.01) |
| *A61Q 19/08* | (2006.01) |

(52) U.S. Cl.
CPC .............. *A61K 8/8147* (2013.01); *A61K 8/06* (2013.01); *A61K 8/11* (2013.01); *A61K 8/26* (2013.01); *A61K 8/345* (2013.01); *A61K 8/675* (2013.01); *A61K 8/731* (2013.01); *A61K 8/737* (2013.01); *A61K 8/8152* (2013.01); *A61K 8/89* (2013.01); *A61K 8/891* (2013.01); *A61K 8/893* (2013.01); *A61K 8/894* (2013.01); *A61K 8/91* (2013.01); *A61Q 5/12* (2013.01); *A61Q 17/04* (2013.01); *A61Q 19/00* (2013.01); *A61K 2800/48* (2013.01); *A61K 2800/52* (2013.01); *A61K 2800/546* (2013.01); *A61K 2800/594* (2013.01); *A61Q 15/00* (2013.01); *A61Q 19/02* (2013.01); *A61Q 19/08* (2013.01)

(58) Field of Classification Search
CPC .... A61Q 17/04; A61Q 19/00; A61K 2800/48; A61K 2800/52; A61K 8/731; A61K 8/89; A61K 8/91; A61K 2800/546; A61K 2800/594; A61K 8/06; A61K 8/25

See application file for complete search history.

(56) References Cited

U.S. PATENT DOCUMENTS

| | | | |
|---|---|---|---|
| 6,039,935 A | 3/2000 | Mohammadi | |
| 6,497,891 B2 | 12/2002 | Bara | |
| 8,252,271 B2 | 8/2012 | Singer | |
| 2005/0053561 A1 | 3/2005 | Suginaka | |
| 2008/0139453 A1 | 6/2008 | Yoshimi | |
| 2008/0145436 A1 | 6/2008 | Lorant | |
| 2009/0035237 A1* | 2/2009 | Maes ....................... | A61K 8/06 424/59 |
| 2010/0322880 A1* | 12/2010 | Rudolph ............... | C07D 307/62 424/59 |
| 2010/0322983 A1 | 12/2010 | Griffiths-Brophy | |
| 2010/0330018 A1 | 12/2010 | Lorant | |
| 2011/0034408 A1* | 2/2011 | Lorant ................. | A61K 8/8158 514/54 |
| 2013/0224133 A1* | 8/2013 | Romanhole ........... | A61K 8/062 424/59 |

FOREIGN PATENT DOCUMENTS

| | | |
|---|---|---|
| EP | 1902704 A1 | 11/2013 |
| GB | 2422605 A | 8/2006 |
| JP | 63208508 | 8/1988 |
| JP | H06157253 | 6/1994 |
| JP | 2011219383 | 11/2011 |

OTHER PUBLICATIONS

Yamaguchi (Journal of the Society of Rheology, Japan, 2014, vol. 42, pp. 129-133).*
IPRP PCT/US2013/032922; International Filing Date Mar. 19, 2013; 9 pages.
International Search Report PCT/US2013/032922; dated Mar. 19, 2013.

* cited by examiner

*Primary Examiner* — Mark V Stevens
(74) *Attorney, Agent, or Firm* — John G. Powell; S. Robert Chuey

(57) ABSTRACT

A thickened aqueous composition containing from about 0.01% to about 10%, by weight, of an superabsorbent polymer, from about 0.1% to about 20%, of a silicone elastomer; and from about 20% to about 98% of water.

19 Claims, No Drawings

SUPERABSORBENT POLYMERS AND SILICONE ELASTOMER FOR USE IN SKIN CARE COMPOSITIONS

FIELD OF THE INVENTION

The present invention relates to the combination of superabsorbent polymers and silicone elastomers for use in improving the look and stability of skin care products.

BACKGROUND OF THE INVENTION

Skin care composition and methods of emulsifying them are known. But there is a continuing need for compositions that look and feel better and are more stable over time. This is especially critical when the skin care composition is a protective composition such as a sunscreen. Consumers of these products are continually looking for newer and longer lasting compositions.

Emulsifying systems for skin care compositions are known. But as new materials, actives and emulsifiers are developed, it is largely up to skin care composition formulators to determine the best methods to blend these into consumer products in a way that delights consumers, but has superior properties to existing formulae. Thus, as each new active ingredient or composition enhancer is developed, there exists an ongoing need to find the optimal blend of ingredients and actives to develop entirely new skin care compositions that have superior qualities over existing formulae.

SUMMARY OF THE INVENTION

The present invention relates to a thickened aqueous composition containing from about 0.01% to about 10%, by weight, of an superabsorbent polymer, from about 0.1% to about 20%, of a silicone elastomer; and from about 20% to about 98% of water.

The present invention provides better stability over time than aqueous systems thickened with conventional thickener systems. The compositions of this invention are also less shiny, which when applied to human skin provide a less reflective coating which tends to make the skin look smoother.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the epidermis.

"Keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Non-UV" means a material not recognized by a skilled artisan in the field of sunscreen formulation to be a dermatologically acceptable UV active absorbing material.

"UV active" means a material recognized by a skilled artisan in the field of sunscreen formulation to be a dermatologically acceptable UV active absorbing material. Such UV actives may be described as being UV-A and/or UV-B active agents. Approval by a regulatory agency is generally required for inclusion of active agents in formulations intended for human use. Those active agents which have been or are currently (per 21 C.F.R. part 352) approved by the U.S. Food and Drug Administration as acceptable for use in over-the counter sunscreen drug products include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the U.S. but are approved for over the counter use in other regions or countries such as Europe (per European Commission's Cosmetic Directive Regulation), Japan, China, Australia, New Zealand, or Canada include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, his diethylamino hydroxybenzoyl benzoate, his benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved materials is currently expanding, those of ordinary skill will recognize that the invention is not limited to UV actives currently approved for human use but are readily applicable to those that may be allowed in the future.

"Leave-on," in reference to compositions, means compositions intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying or other processing surfactants that are not intended to provide any significant cleansing benefits when applied topically to the skin.

"Derivatives" means an ester, ether, amide, hydroxy, and/or salt structural analogue of the relevant compound.

"Soluble" means at least about 0.1 g of solute dissolves in 100 ml of solvent, at 25° C. and 1 atm of pressure.

Superabsorbent Polymer

The term "superabsorbent polymer" is understood to mean a polymer which is capable, in its dry state, of spontaneously absorbing at least 20 times its own weight of aqueous fluid, in particular of water and especially of distilled water. Such superabsorbent polymers are described in the work "Absorbent Polymer Technology, Studies in Polymer Science 8" by L. Brannon-Pappas and R. Harland, published by Elsevier, 1990.

These polymers have a high capacity for absorbing and retaining water and aqueous fluids. After absorption of the aqueous liquid, the particles of the polymer thus impregnated with aqueous fluid remain insoluble in the aqueous fluid and thus retain their separated particulate state.

Superabsorbent polymers are now commonly made from the polymerization of acrylic acid blended with sodium hydroxide in the presence of an initiator to form a polyacrylic acid sodium salt (sometimes referred to as sodium polyacrylate). This polymer is the most common type of superabsorbent polymers made in the world today. Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile to name a few. The latter is one of the oldest superabsorbent polymers forms created. Today superabsorbent polymers are made using one of three primary methods; gel, polymerization, suspension polymerization or solution polymerization.

Gel Polymerization involves a mixture of frozen acrylic acid, water, cross-linking agents and UV initiator chemicals are blended and placed either on a moving belt or in large tubs. The liquid mixture then goes into a "reactor" which is a long chamber with a series of strong UV lights. The UV radiation drives the polymerization and cross-linking reactions. The resulting "logs" are sticky gels containing 60-70% water. The logs are shredded or ground and placed in various sorts of driers. Additional cross-linking agent may be sprayed on the particles' surface; this "surface cross-linking" increases the product's ability to swell under pressure—a property measured as Absorbency Under Load (AUL) or Absorbency Against Pressure (AAP). The dried polymer particles are then screened for proper particle size distribution and packaging. The Gel Polymerization (GP) method is currently the most popular method for making the sodium polyacrylate superabsorbent polymers now used in baby diapers and other disposable hygienic articles.

Solution polymers, those made by solution polymerization, offer the absorbency of a granular polymer supplied in solution form. Solutions and can be diluted with water prior to application. Can coat most substrates or used to saturated. After drying at a specific temperature for a specific time, the result is a coated substrate with superabsorbent functionality. For example, this chemistry can be applied directly onto wires & cables, though it is especially optimized for use on components such as rolled goods or sheeted substrates.

Solution based polymerization is commonly used today for SAP manufacture of copolymers—particularly—those with the toxic acrylamide monomer. This process is efficient and generally has a lower capital cost base. The solution process uses a water based monomer solution to produce a mass of reactant polymerized gel. The polymerization's own reaction energy (exothermic) is used to drive much of the process, helping reduce manufacturing cost. The reactant polymer gel is then chopped, dried and ground to its final granule size. Any treatments to enhance performance characteristics of the SAP are usually accomplished after the final granule size is created.

Superabsorbent polymers can also be made by suspension polymerization. This process suspends the water-based reactant in a hydrocarbon-based solvent. The net result is that the suspension polymerization creates the primary polymer particle in the reactor rather than mechanically in post-reaction stages. Performance enhancements can also be made during, or just after, the reaction stage.

The superabsorbent polymer can have a water-absorbing capacity ranging from 20 to 2000 times its own weight (i.e., 20 g to 2000 g of water absorbed per gram of absorbent polymer), preferably from 30 to 1500 times and better still ranging from 50 to 1000 times, and even more preferably 400 times. These water-absorbing characteristics are defined at standard temperature (25° C.) and pressure (760 mm Hg, i.e. 100 000 Pa) conditions and for distilled water. The value of the water-absorbing capacity of a polymer can be determined by dispersing 0.5 g of polymer(s) in 150 g of a water solution, by waiting 20 minutes, by filtering the nonabsorbed solution through a 150 µm filter for 20 minutes and by weighing the nonabsorbed water.

The superabsorbent polymer used in the composition of the invention is preferably provided in the form of particles which, once hydrated, swell with the formation of soft beads having a number-average diameter of 10 µm to 1000 µm.

The superabsorbent polymers used in the present invention are preferably crosslinked acrylic homo- or copolymers which are preferably neutralized and which are provided in the particulate form.

Mention may in particular be made of the polymers chosen from: crosslinked sodium polyacrylates, such as, for example, those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, Aqua Keep 10 SH NFC, sodium acrylate crosspolymer-2, provided by Sumitomo Seika, starches grafted by an acrylic polymer (homopolymer or copolymer) and in particular by sodium polyacrylate, such as those sold under the names Sanfresh ST-100C, ST100MC and IM-300MC by Sanyo Chemical Industries (INCI name: Sodium Polyacrylate Starch), hydrolysed starches grafted by an acrylic polymer (homopolymer or copolymer), in particular the acrylo-acrylamide/sodium acrylate copolymer, such as those sold under the names Water Lock A-240, A-180, B-204, D-223, A-100, C-200 and D-223 by Grain Processing (INCI name: Starch/Acrylamide/Sodium Acrylate Copolymer), Preferably, the superabsorbent polymer is a sodium polyacrylate starch that in its non-swollen state exhibits a number-average size of less than or equal to 100 µm, preferably of less than or equal to 50 µm, for example ranging from 2 µm to 100 µm, with a median particle size of 25, or preferably in the range of about 2 µm to about 40 µm with a median particle size of 12. The viscosity of a solution in 1% water is preferably in the range of 20 to 30 Pas, even more preferably 22 to 29 Pas, at a pH of 4, and in the range of 23 to 28 Pas, at a pH of 7. Preferred superabsorbent polymers include Makimousse 12 and Makimousse 25 supplied by Kobo Products Inc.

The superabsorbent polymer can be present in the composition of the invention in a content as active material ranging, for example, from 0.01 to 10% by weight, preferably from 0.05 to 6% by weight, preferably from 0.1 to 4% by weight, preferentially from 0.1 to 3% by weight, indeed even from 0.1 to 2% by weight, with respect to the total weight of the composition.

Silicone Elastomer

The composition of the present invention comprises a silicone elastomer, useful for reducing the tackiness of the composition and for providing a pleasant feel upon application. One non-limiting example of useful silicone elastomers is crosslinked organopolysiloxane (or siloxane) elastomers, as described in U.S. patent publication 2003/0049212A1. The elastomers may comprise emulsifying and non-emulsifying silicone elastomers. "Emulsifying," as used herein, means crosslinked organopolysiloxane elastomers having at least one polyoxyalkylene (e.g., polyoxyethylene or polyoxypropylene) or polyglycerin moiety, whereas "non-emulsifying" means crosslinked organopolysiloxane elastomers essentially free of polyoxyalkylene or polyglycerin moeities.

The composition of the present invention may comprise from about 0.1% to about 20%, and alternatively from about 0.2% to about 10%, of a non-emulsifying crosslinked organopolysiloxane elastomer. Non-limiting examples of suitable non-emulsifying crosslinked organopolysiloxane elastomers include dimethicone crosspolymers, dimethicone/vinyl dimethicone crosspolymers, and copolymers, derivatives and mixtures thereof, supplied by Dow Corning™ (e.g. DC 9040, 9041, 9045, 8509, 9546, 9506); C30-45 alkyl cetearyl dimethicone crosspolymer, cetearyl dimethicone crosspolymer, and copolymers, derivatives and mixtures thereof, supplied by General Electric™ (e.g. Velvesil™ 125 and Velvesil™ DM); dimethicone/phenyl vinyl dimethicone crosspolymer, vinyl dimethicone/lauryl dimethicone crosspolymer, trifluoropropyl dimethicone/trifluoropropyl divinyldimethicone crosspolymer, and copolymers, derivatives and mixtures thereof, supplied by Shin Etsu™ (KSG-15, -15AP, -16, -17, -18, -41, -42, -43, -44, -51, -103), and the Grant Industries line of elastomers, available as GRANSIL™.

The composition of the present invention may comprise from about 0.1% to about 20%, and alternatively from about 0.2% to about 10%, of an emulsifying crosslinked organopolysiloxane elastomer, described in U.S. Pat. Nos. 5,412,004; 5,837,793; and 5,811,487. Non-limiting examples of suitable emulsifying elastomers include PEG-12 dimethicone crosspolymers, dimethicone/PEG-10/15 crosspolymer, dimethicone/PEG-10 crosspolymer, PEG-15/lauryl dimethicone crosspolymer, trifluoropropyl dimethicone/PEG-10 crosspolymer, dimethicone/polyglycerin-3 crosspolymer, lauryl dimethicone/polyglycerin-3 crosspolymer, all supplied by Shin Etsu™ (KSG-24, -21/210, -31/310, -32/320, -33/330, -34/340, -710, -810, -820, -830, and -840); polyoxyalkylene-modified elastomers formed from divinyl compounds, e.g. siloxane polymers with at least two free vinyl groups bonded via Si—H linkages on a polysiloxane backbone.

Suitable silicone elastomers include many commercial materials. An exemplary polyoxyethylene silicone elastomer includes dimethicone/PEG-10/15 crosspolymer (KSG-210 from Shin-Etsu Chemical Co, Ltd.).

Examples of alkyl-containing polyoxyethylene silicone elastomers include PEG-15 lauryl dimethicone crosspolymer (KSG-310, KSG-320, KSG-330, & KSG-340 from Shin-Etsu Chemical Co., Ltd.).

An example of polyglycerin-modified silicone elastomers includes dimethicone/polyglycerin-3 crosspolymer (KSG-710 from Shin-Etsu Chemical Co., Ltd.).

Examples of alkyl-containing polyglycerin-modified silicone elastomers include lauryl dimethicone/polyglycerin-3 crosspolymer (KSG-810, KSG-820, KSG-830, & KSG-840 from Shin-Etsu Chemical Co., Ltd.).

Examples of polyoxypropylene silicone elastomer includes dimethicone/bis-isobutyl PPG-20 crosspolymer (Dow Corning EL-8050, EL-8051, & EL-8052 from Dow Corning Corp.).

In select embodiments, the silicone elastomer is chosen from alkyl dimethicone/polyglycerin crosspolymers, dimethicone/polyglycerin crosspolymers, dimethicone/poly(propylene glycol) crosspolymers, dimethicone/poly(ethylene glycol) crosspolymers, alkyl dimethicone/poly(propylene glycol) crosspolymers, alkyl dimethicone/poly(ethylene glycol) crosspolymers, and alkyl dimethicone crosspolymers.

Additional Thickening Agents

The composition of the present invention may include one or more additional thickening agents. The composition of the present invention may comprise from about 0.1% to about 5%, or, alternatively, from about 0.2% to about 2%, of a thickening agent when present. Suitable classes of thickening agents include but are not limited to carboxylic acid polymers, polyacrylamide polymers, sulfonated polymers, copolymers thereof, hydrophobically modified derivatives thereof, and mixtures thereof.

One preferred thickener for use in the present invention is an acrylate cross linked silicone copolymer network (also sometimes referred to as "polyacrylate siloxane copolymer network") and its method of making are fully disclosed in US Patent Publication 2008/0051497 A1, Lu et. al, which published on Feb. 28, 2008. These copolymers comprise the reaction product of:

a) $M_a M^H_{b-h-k} M^{PE}_h M^E_k D_c D^H_{d-i-j} D^{PE}_i D^E_j TeT^H_{f-j-m} T^{PE}_j T^E_m Q_g$ and b) a stoichiometric or super-stoichiometric quantity of acrylate where:

$M = R^1 R^2 R^3 SiO_{1/2}$;

$M^H = R^4 R^5 HSiO_{1/2}$;

$M^{PE} = R^4 R^5 (-CH_2 CH(R^9)(R^{10}))_n O(R^{11})_o (C_2H_4O)_o (C_3H_6O)_q (C_4H_8O)_r R^{12}) SiO_{1/2}$;

$M^E = R^4 R^5 (-R^{17} R^{18} C-CR^{16} Q_s Q_t R^{15}(COC) R^{13} R^{14}) SiO_{1/2}$ $D = R^6 R^7 SiO_{2/2}$; and $D^H = R^8 HSiO_{2/2}$ $D^{PE} = R^8 (-CH_2 CH(R^9)(R^{10}))_n O(R^{11})_o (C_2H_4O)_p (C_3H_6O)_q (C_4H_8O)_r R^{12}) SiO_{2/2}$ $D^E = R^8 (-R^{17} R^{18} C-CR^{16} Q_s Q_t R^{15}(COC)-R^{13} R^{14}) SiO_{2/2}$.

$T^H = HSiO_{3/2}$;

$T^{PE} = (-CH_2 CH(R^9)(R^{10}))_n O(R^{11})_o (C_2H_4O)_p (C_3H_6O)_q (C_4H_8O)_r R^{12}) SiO_{3/2}$;

$T^E = (-R^{17} R^{18} C-CR^{16} Q_s Q_t R^{15}(COC) R^{13} R^{14}) SiO_{3/2}$; and $Q = SiO_{4/2}$;

where $R^1$, $R^2$, $R^3$, $R^4$, $R^5$, $R^6$, $R^7$, $R^8$ and $R^9$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of —$C_2H_4O$—, —$C_3H_6O$—, and —$C_4H_8O$—; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms.

Q is a di- or trivalent hydrocarbon radical having from one to sixty carbon atoms, $Q_s$ is a divalent hydrocarbon radical having from one to sixty carbon atoms subject to the limitation that when Q is trivalent $R^{14}$ is absent and $Q_s$ forms a bond with the carbon bearing $K^{13}$ where $K^{16}$ and $R^{18}$ may be either cis- or trans- to each other; the subscript a may be zero or positive subject to the limitation that when the subscript a is zero, b must be positive; the subscript b may be zero or positive subject to the limitation that when b is zero, the subscript a must be positive; the subscript c is positive and has a value ranging from about 5 to about 1,000; the subscript d is positive and has a value ranging from about 3 to about 400; the subscript e is zero or positive and has a value ranging from 0 to about 50; the subscript f is zero or positive and has a value ranging from 0 to about 30; the subscript g is zero or positive and has a value ranging from 0 to about 20; the subscript h is zero or positive and has a value ranging from 0 to about 2 subject to the limitation that the sum of the subscripts h, i and j is positive; the subscript i is zero or positive and has a value ranging from 0 to about 200 subject to the limitation that the sum of the subscripts h, i and j is positive; the subscript j is zero or positive and has a value ranging from 0 to about 30 subject to the limitation that the sum of the subscripts h, i and j is positive; the subscript k is zero or positive and has a value ranging from 0 to about 2 subject to the limitation that the sum of the subscripts k, 1 and m is positive; the subscript 1 is zero or positive and has a value ranging from 0 to about 200 subject to the limitation that the sum of the subscripts k, 1 and m is positive; the subscript m is zero or positive and has a value ranging from 0 to about 30 subject to the limitation that the sum of the subscripts k, 1 and m is positive; the subscript n is zero or one; the subscript o is zero or one; the subscript p is zero or positive and has a value ranging from 0 to about 100 subject to the limitation that (p+q+r)>0; the subscript q is zero or positive and has a value ranging from 0 to about 100 subject to the limitation that (p+q+r)>0; the subscript r is zero or positive and has a value ranging from 0 to about 100 subject to the limitation that (p+q+r)>0; the subscript s is zero or one; the subscript t is zero or one; and c) a free radical initiator.

As used herein, integer values of stoichiometric subscripts refer to molecular species and non-integer values of stoichiometric subscripts refer to a mixture of molecular species on a molecular weight average basis, a number average basis or a mole fraction basis. The phrases sub-stoichiometric and super stoichiometric refer to relationships between reactants. Sub stoichiometric refers to a quantity of reactant that is less than the quantity of reactant required for full stoichiometric reaction of a substrate moiety with that reactant. Super stoichiometric refers to a quantity of reactant that is more than that quantity of reactant required for full stoichiometric reaction of a substrate moiety with that reactant. As used herein "super stoichiometric" can under some circumstances be equivalent to an excess that is either a stoichiometric excess, i.e. a whole number multiple of a stoichiometric quantity, or a non-stoichiometric excess.

As used herein the word "acrylate" is a collective noun for the following chemical species: acrylic acid and methacrylic acid or ester derivatives thereof such as methyl, ethyl, butyl, amyl, 2-ethylhexyl, cyclohexyl, vinyl, ally, hydroxyethyl, perfluoroethyl, isobornyl, phenoxyethyl, tetraethylene glycol, tripropylene glycol, trimethylolpropane, polyoxyalkylene, organic modified polysiloxane (for example, the acrylated hydrophilic polysiloxane used as the emulsion precursor in U.S. Pat. No. 6,207,782), anionic acrylates/methacrylates such as sulfate, sulfonate or phosphate functionalized acrylate or mixtures thereof and any catalyst necessary for reaction with the epoxy or oxirane group. A single acrylate or various combinations of acrylates and methacrylates may be employed. A preferred acrylate cross linked silicone copolymer is a polyacrylate cross polymer from Momentive.

Suitable thickening agents include carboxylic acid polymers such as the carbomers (e.g., the CARBOPOL® 900 series such as CARBOPOL® 954). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as CARBOPOL® 1342, CARBOPOL® 1382, PEMULEN TR-1, and PEMULEN TR-2, from Noveon, Inc.

Other suitable thickening agents include the polyacrylamide polymers and copolymers. An exemplary polyacrylamide polymer has the CTFA designation "polyacrylamide and isoparaffin and laureth-7" and is available under the trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500 W, SSSA100H, from Lipo Chemicals, Inc., (Patterson, N.J.).

Other suitable thickening agents useful herein are sulfonated polymers such as the CTFA designated sodium polyacryloyldimethyl taurate available under the trade name Simulgel 800 from Seppic Corp. and Viscolam At 100 P available from Lambeth S.p.A. (Gallarate, Italy). Another commercially available material comprising a sulfonated polymer is Sepiplus 400 available from Seppic Corp.

"Gum" is a broadly defined term in the art. Gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, derivatives thereof and mixtures thereof.

Natural gums are polysaccharides of natural origin, capable of causing a large viscosity increase in solution, even at small concentrations. They can be used as thickening agents, gelling agents, emulsifying agents, and stabilizers. Most often these gums are found in the woody elements of plants or in seed coatings. Natural gums can be classified according to their origin. They can also be classified as uncharged or ionic polymers (polyelectrolytes), examples of which include the following. Natural gums obtained from seaweeds, such as: agar; alginic acid; sodium alginate; and carrageenan. Natural gums obtained from non-marine botanical resources include: gum arabic, from the sap of *Acacia* trees; gum ghatti, from the sap of Anogeissus trees; gum tragacanth, from the sap of *Astragalus* shrubs; karaya gum, from the sap of Sterculia trees. Examples of uncharged gums include: guar gum, from guar beans, locust bean gum, from the seeds of the carob tree; beta-glucan, from oat or barley bran; chicle gum, an older base for chewing gum obtained from the chicle tree; dammar gum, from the sap of Dipterocarpaceae trees; glucomannan from the konjac plant; mastic gum, a chewing gum from ancient Greece obtained from the mastic tree; psyllium seed husks, from the *Plantago* plant; spruce gum, a chewing gum of American Indians obtained from spruce trees; tara gum, from the seeds of the tara tree. Natural gums produced by bacterial fermentation include gellan gum and xanthan gum.

Clays may be useful to provide structure or thickening. Suitable clays can be selected, e.g., from montmorillonites, bentonites, hectorites, attapulgites, sepiolites, laponites, silicates and mixtures thereof. Suitable water dispersible clays include bentonite and hectorite (such as Bentone EW, LT from Rheox); magnesium aluminum silicate (such as Veegum from Vanderbilt Co.); attapulgite (such as Attasorb or Pharamasorb from Engelhard, Inc.); laponite and montrnorillonite (such as Gelwhite from ECC America); and mixtures thereof.

Suitable thickening agents include cellulose and modified cellulosic compositions such as, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers some portion of the hydroxy groups of the cellulose polymer are hydroyxalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Oil Phase

The thickened aqueous phase of this invention may be combined with, or emulsified with an oil phase to form an oil-in-water emulsion or a water-in-oil-in-water emulsion. Oils may be used to solubilize, disperse, or carry materials that are not suitable for water or water soluble solvents. Oils may be fluid at room temperature. The oils may be volatile or nonvolatile. "Nonvolatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable. Suitable oils include hydrocarbons, esters, amides, ethers, silicones, and mixtures thereof.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, butyloctyl salicylate, phenylethyl benzoate, dicaprylyl carbonate, dioctyl malate, dicaprylyl maleate, isononyl isononanoate, propylene glycol dicaprate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the personal care composition include those known as polyhydric alcohol esters and glycerides.

Other suitable oils include amides. Amides include compounds having an amide functional group while being liquid at 25° C. and insoluble in water. Suitable amides include, but are not limited to, N-acetyl-N-butylaminopropionate, isopropyl N-lauroylsarcosinate, butylphthalimide, isopropylphthalimide, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include, but are not limited to, $C_{4-20}$ alkyl ethers of polypropylene glycols, and di-$C_{8-30}$ alkyl ethers. Suitable examples of these materials include PPG-14 butyl ether, PPG-15 stearyl ether, PPG-11 stearyl ether, dioctyl ether, dodecyl octyl ether, and mixtures thereof.

Suitable silicone oils include polysiloxanes. Polylsiloxanes may have a viscosity of from about 0.5 to about 1,000,000 centistokes at 25° C. Such polysiloxanes can be represented by the general chemical formula:

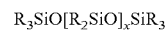

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100, 000, and 300,000 centistokes.

Suitable dimethicones include those represented by the chemical formula:

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

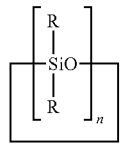

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6). UV Actives The compositions of this invention may comprise a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010. The composition may comprise from may comprise an amount of UV active prescribed or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. In particular embodiments, the composition comprises from about 1%, 2%, or 3% to about 40%, 30%, or 20%, by weight of the composition, UV active. In another embodiment, the composition may comprise a sufficient about of UV active to yield a Sun Protection Factor of at least about 15, 30 45, or 50. SPF testing is conventional and well understood in the art. A suitable SPF test is prescribed in 21 C.F.R. 352, Subpart D.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl salicylate, homomenthyl salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures of these compounds.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), ethylhexyl triazone (commercially available as Uvinul® T 150 from BASF), drometrizole trisiloxane (marketed as Mexoryl XL by L'Oreal), sodium dihydroxy dimethoxy disulfobenzophenone (i.e., benzophenone-9, commercially available as Uvinul® DS 49 from BASF), diethylamino hydroxybenzoyl hexyl benzoate (commercially available as Uvinul® A Plus from BASF), diethylhexyl butamido triazone (i.e., Iscotrizinol, commercially available as Uvasorb® HEB by 3V Sigma), polysilicone-15 (i.e., commercially available as PARSOL® SLX from DSM), isoamyl p-methoxycinnamate (i.e., amiloxate, commercially available as Neo Heliopan® E 1000 from Symrise), and mixtures thereof.

The UV actives of the present invention may be encapsulated. Examples of commercially available encapsulated sunscreen actives include, but are not limited to: Eusolex UV-Pearls 2292 (Merck/EMD Chemicals), which includes water, ethylhexyl methoxycinnamate, silica, phenoxyethanol, PVP, chlorphenesin, disodium EDTA, and BHT; Silasoma ME (Seiwa Kasei Co., Ltd), which includes water, polysilicone-14, and ethylhexyl methoxycinnamate; Silasoma MEA (Seiwa Kasei Co., Ltd), which includes water, polysilicone-14, ethylhexyl methoxycinnamate, and butyl methoxydibenzoylmethane; Silasoma MEP(S) (Seiwa Kasei Co., Ltd), which includes water, ethylhexyl methoxycinnamate, diethylamino hydroxybenzoyl hexyl benzoate, and polysilicone-14; Suncaps 664 (Particle Sciences, Inc.), which includes, ethylhexyl methoxycinnamate, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; Suncaps 903 (Particle Sciences, Inc.), which includes ethylhexyl methoxycinnamate, benzophenone-3, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; UV Pearls OMC (Sol Gel Technologies), which includes ethylhexyl methoxycinnamate, and silica; OMC-BMDBM (Sol Gel Technologies), which includes ethylhexyl methoxycinnamate, butyl methoxydibenzoylmethane, and silica; Tinosorb S Aqua (BASF), which includes, bis-ethylhexyloxyphenol methoxyphenyl triazine, and polymethyl methacrylate; Hybrid ABOS (Kobo), which includes, polymethylmethacrylate, butyl methoxydibenzoylmethane, and octyl salicylate; and Hybrid ABOMC (Kobo), which includes polymethylmethacrylate, butyl methoxydibenzoylmethane, and ethylhexyl methoxycinnamate.

Photostabilizer

When UV actives are used in the compositions of this invention, they may comprise a photostabilizer. The composition may comprise from about 0.0001%, 0.001%, 0.01%, 0.05%, 0.1%, 0.5%, or 1% to about 20%, 10%, 7%, or 5%, by weight of the composition, of one or more suitable photostabilizer.

A suitable photostabilizer is alpha-cyanodiphenylacrylate is as disclosed in U.S. Pat. No. 7,713,519. The alpha-cyanodiphenylacrylate may have the general formula:

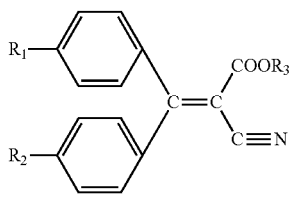

wherein one or both of R1 and R2 is independently a straight or branched chain C1-30 alkoxy radical and any non-alkoxy R1 or R2 radical is hydrogen; and R3 is a straight or branched chain C1-30 alkyl. Alternately, one or both of R1 and R2 is independently a C1-8 alkoxy radical and any non-alkoxy R1 or R2 radical is hydrogen; and R3 is a straight of branched chain C2-20 alkyl. Alternately, one or both of R1 and R2 is independently methoxy, and any non-methoxy R1 or R2 is hydrogen; and R3 is a straight or branched chain C2-20 alkyl.

A suitable alpha-cyanodiphenylacrylate is ethylhexyl methoxycrylene, or 2-ethylhexyl 2-cyano-3-(4-methoxyphenyl)-3-phenylpropenoate, wherein R1 is methoxy, R2 is hydrogen, and R3 is 2-ethylhexyl. This material is available from Hallstar Company under trade name Solastay® S1.

Another suitable photostabilizer includes diesters or polyesters of naphthalene dicarboxylic acid as disclosed in U.S. Pat. Nos. 5,993,789, 6,113,931, 6,126,925 and 6,284,916. Suitable diesters or polyesters of naphthalene dicarboxylic acid may have the following formula:

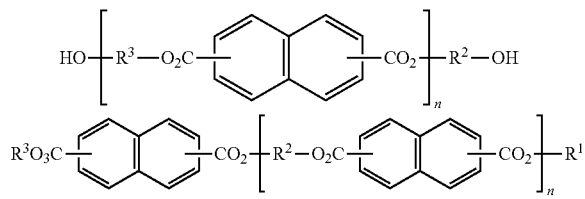

or
wherein each $R^1$ independently is an alkyl group having 1 to 22 carbon atoms, or a diol having the formula HO—$R^2$—OH, or a polyglycol having the formula HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, 1 to about 10, or 2 to about 7. A suitable diester of naphthalene dicarboxylic acid is diethylhexyl 2,6-naphthalate available as Corapan® TQ from Symrise.

Another suitable photostabilizer is 4-hydroxybenzylidenemalonate derivatives or 4-hydroxycinnamate derivatives. Suitable materials may have the following formula:

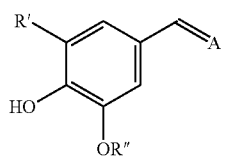

wherein A is a chromophoric group that absorbs UV-radiation, comprises one divalent group or two monovalent groups with at least one group having carbonyl (C=O) functionality; R' is hydrogen, a linear or branched $C_1$-$C_8$ alkyl radical or a linear or branched $C_1$-$C_8$ alkoxy radical; and R" is a linear or branched $C_1$-$C_8$ alkyl radical. Exemplary compounds include ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. A particularly suitable compound is diethylhexyl syringylidenemalonate (INCI name) available under the tradename Oxynex® ST from EMD Chemicals, Inc. Additional suitable 4-hydroxybenzylidenemalonate derivatives or 4-hydroxycinnamate derivatives are disclosed in U.S. Pat. No. 7,357,919 and U.S. Patent Application Publication No. 2003/0108492A1 and US2003/0157035A.

Other suitable photostabilizers include a 2-pyrrolidinone-4-carboxy ester compounds as described in U.S. Patent Application Publication No. 2010/0183529; silicon-containing s-triazines substituted with two aminobenzoate or aminobenzamide groups as described in U.S. Patent Application Publication No. 2008/0145324; fluorene derivatives as described in U.S. Patent Application Publications Nos. 2004/00579912, 2004/00579914, 200/00579916, and 2004/062726; piperidinol salts as described in U.S. Patent Application Publications No. 2005/0220727 including tris(tetramethylhydroxypiperidinol) citrate sold under the tradename Tinogard® Q by Ciba; and arylalkyl amides and esters as described in U.S. Patent Application Publication No. 2008/0019930.

Other suitable photostabilizers are listed in the functional category of "Light Stabilizers" in the Personal Care Product Council's *International Cosmetic Ingredient Dictionary and Handbook*, Thirteenth Edition, 2010.

Emulsifiers

The compositions of this invention may comprise an emulsifier. An emulsifier is particularly suitable when the phase is in the form of an emulsion or if immiscible materials are being combined. The phase may comprise from about 0.01%, 0.05%, or 0.1% to about 10%, 5%, or 2% emulsifier. Emulsifiers may be nonionic, anionic or cationic. Non-limiting examples of emulsifiers are disclosed in U.S.

Pat. Nos. 3,755,560, 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Silicone emulsifiers may be use in the phase. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin Etsu.

Fatty Alcohols

The compositions of this invention may comprise one or more fatty alcohols. Fatty alcohols typically include monohydric alcohols having 8-22 carbon atoms although longer chain alcohols in excess of 30 carbons may be used. The fatty alcohols may be saturated or unsaturated. The fatty alcohols may be straight or branched. In particular, the phase may comprise straight chain, saturated fatty alcohol with a terminal hydroxyl. Suitable fatty alcohols include decyl alcohol, lauryl alcohol, myristyl alcohol, cetyl alcohol, stearyl alcohol, isostearyl alcohol, cetearyl alcohol, icosyl alcohol, behenyl alcohol. The phase may comprise from about 0.1%, 0.5%, 1%, 1.5%, 2%, 3%, 5% to about 5%, 7.5%, 10%, 15%, 20% of fatty alcohol.

Skin Care Active

The compositions of the present invention may comprise at least one additional skin care active. Many skin care actives may provide more than one benefit, or operate via more than one mode of action; therefore, classifications herein are made for the sake of convenience and are not intended to limit the active to that particular application or applications listed.

Vitamins

The compositions of the present invention may comprise from about 0.0001% to about 50%, alternatively from about 0.001% to about 10%, and alternatively from about 0.01% to about 5%, of one or more vitamins. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, C1-C18 nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition comprises a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

Peptides and Peptide Derivatives

The compositions of the present invention may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EE-MQRR; Argireline®), and Cu-histidine-glycine-glycine (Cu-HGG, also known as IAMIN®).

The compositions may comprise from about $1 \times 10^{-7}$% to about 20%, alternatively from about $1 \times 10^{-6}$% to about 10%, and alternatively from about $1 \times 10^{-5}$% to about 5% of the peptide.

Sugar Amines

The compositions of the present invention may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Sugar amine compounds useful in the present invention include, for example, N-acetyl-glucosamine, and also those described in PCT Publication WO 02/076423 and U.S. Pat. No. 6,159,485, issued to Yu, et al. In one embodiment, the composition comprises from about 0.01% to about 15%, alternatively from about 0.1% to about 10%, and alternatively from about 0.5% to about 5%, of the sugar amine.

The compositions of the present invention further may comprise non-vitamin antioxidants and radical scavengers, hair growth regulators, flavonoids, minerals, preservatives, phytosterols and/or plant hormones, protease inhibitors, tyrosinase inhibitors, anti-inflammatory agents and N-acyl amino acid compounds.

Suitable non-vitamin antioxidants and radical scavengers include, but are not limited to, BHT (butylated hydroxy toluene), L-ergothioneine (available as THIOTANE™); tetrahydrocurcumin, cetyl pyridinium chloride, carnosine, diethylhexyl syrinylidene malonate (available as OXYNEX™), hexadec-8-ene-1,16-dicarboxylic acid (octadecene dioic acid; ARLATONE™ Dioic DCA from Uniqema), ubiquinone (co-enzyme Q10), tea extracts including green tea extract, yeast extracts or yeast culture fluid (e.g., Pitera®), and combinations thereof.

Suitable hair growth regulators include, but are not limited to, hexamidine, butylated hydroxytoluene (BHT), hexanediol, panthenol and pantothenic acid derivates, their isomers, salts and derivatives, and mixtures thereof.

Suitable minerals include zinc, manganese, magnesium, copper, iron, selenium and other mineral supplements. "Mineral" is understood to include minerals in various oxidation states, mineral complexes, salts, derivatives, and combinations thereof.

Suitable examples of plant sterols (phytosterols) and/or plant hormones include, but are not limited to, sitosterol, stigmasterol, campesterol, brassicasterol, kinetin, zeatin, and mixtures thereof.

Suitable protease inhibitors include, but are not limited to, hexamidine, vanillin acetate, menthyl anthranilate, soybean trypsin inhibitor, Bowman-Birk inhibitor, and mixtures thereof.

Suitable tyrosinase inhibitors include, but are not limited to, sinablanca (mustard seed extract), tetrahydrocurcumin, cetyl pyridinium chloride, and mixtures thereof.

Suitable anti-inflammatory agents include, but are not limited to, glycyrrhizic acid (also known as glycyrrhizin, glycyrrhixinic acid, and glycyrrhetinic acid glycoside), glycyrrhetenic acid, other licorice extracts, and combinations thereof.

Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE® from Seppic (France).

Other useful skin care actives include moisturizing and/or conditioning agents, such as glycerol, petrolatum, caffeine, and urea; yeast extracts (for example, Pitera™); dehydroepiandrosterone (DHEA), its analogs and derivatives; exfoliating agents, including alpha- and beta-hydroxyacids, alpha-keto acids, glycolic acid and octanoyl salicylate; antimicrobial agents; antidandruff agents such as piroctone olamine, 3,4,4'-trichlorocarbanilide (trichlosan), triclocarban and zinc pyrithione; dimethyl aminoethanol (DMAE); creatine; skin lightening agents such as kojic acid, mulberry extract, hydroquinone, arbutin, and deoxy-arbutin; (sunless) tanning agents, such as dihydroxy acetone (DHA); isomers, salts, and derivatives of any of the foregoing; and mixtures thereof.

Humectants

The compositions of the present invention may include one or more humectants. The composition of the present invention may comprise from about 1% to about 30%; alternatively, from about 2% to about 20%; or, alternately, from about 3% to about 15% of the humectant, when present. An exemplary class of humectants is polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; hexylene glycol; butylene glycol (e.g., 1,3-butylene glycol); pentylene glycol; hexane triol (e.g., 1,2,6-hexanetriol); glycerine; ethoxylated glycerine; and propoxylated glycerine.

Other suitable humectants include sodium 2-pyrrolidone-5-carboxylate, guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol; sodium pyroglutamate (NaPCA), water-soluble glyceryl poly(meth)acrylate lubricants (such as Hispagel®) and mixtures thereof.

Particulate Material

The compositions of the present invention may comprise from about 0.001% to about 40%, alternatively from about 1% to about 30%, and alternatively from about 2% to about 20%, of one or more particulate materials and/or cosmetic powders. Non-limiting examples of suitable powders include inorganic powders (for example, iron oxides, titanium dioxides, zinc oxides, silica), organic powders, composite powders, optical brightener particles, and mixtures of any of the foregoing. These particulates can, for instance, be platelet shaped, spherical, elongated or needle-shaped, or irregularly shaped; surface coated or uncoated; porous or non-porous; charged or uncharged; and can be added to the current compositions as a powder or as a pre-dispersion. In one embodiment, the particulate material is hydrophobically coated.

Suitable organic powders particulate materials include, but are not limited, to polymeric particles chosen from the methylsilsesquioxane resin microspheres, for example, Tospearl™ 145A, (Toshiba Silicone); microspheres of polymethylmethacrylates, for example, Micropearl™ M 100 (Seppic); the spherical particles of crosslinked polydimethylsiloxanes, for example, Trefil™ E 506C or Trefil™ E 505C (Dow Corning Toray Silicone); sphericle particles of polyamide, for example, nylon-12, and Orgasol™ 2002D Nat C05 (Atochem); polystyrene microspheres, for example Dyno Particles, sold under the name Dynospheres™, and ethylene acrylate copolymer, sold under the name Flo-Bead™ EA209 (Kobo); aluminium starch octenylsuccinate, for example Dry Flo™ (Akzo Nobel); polymethyl silsesquioxane coated tapioca particles, for example Dry Flo TS™ (Akzo Nobel); microspheres of polyethylene, for example Microthene™ FN510-00 (Equistar), silicone resin, polymethylsilsesquioxane silicone polymer, platelet shaped powder made from L-lauroyl lysine, and mixtures thereof.

The composition of the present invention further may comprise interference pigments, including hydrophobically-modified interference pigments. Herein, "interference pigments" means thin, platelike layered particles having two or more layers of controlled thickness. The layers have different refractive indices that yield a characteristic reflected color from the interference of typically two, but occasionally more, light reflections, from different layers of the platelike particle. One example of interference pigments are micas layered with about 50-300 nm films of $TiO_2$, $Fe_2O_3$, silica, tin oxide, and/or $Cr_2O_3$ and include pearlescent pigments. Intereference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls™) and Eckart (Prestige™). In one embodiment, the average diameter of the longest side of the individual particles of interference pigments is less than about 75 microns, and alternatively less than about 50 microns.

Colorants

The composition of the present invention may comprise from about 0.00001% to about 25%, and alternatively from about 0.01% to about 10%, of a colorant. Non-limiting classes of suitable colorants include, but are not limited to organic and/or inorganic pigments, natural and/or synthetic dyes, lakes, including FD&C and/or D&C lakes and blends, and mixtures of any of the foregoing.

Non-limiting examples of suitable colorants include iron oxides, ferric ammonium ferrocyanide, manganese violet, ultramarine blue, and chromium oxide, phthalocyanine blue and green pigment, encapsulated dyes, inorganic white pigments, for example $TiO_2$, $ZnO$, or $ZrO_2$, FD&C dyes, D&C dyes, and mixtures thereof.

Oil Control Agents

The compositions of the present invention may comprise one or more compounds useful for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

EXAMPLES

The following are examples of aqueous compositions that are prepared by first combining the water phase ingredients and mixing until uniform. Next, the thickeners are added and the composition is again mixed until uniform. Finally, the elastomer is added and composition is mixed and/or milled (e.g., with a rotor-stator mill) until uniform.

| | Example | | | | | | |
|---|---|---|---|---|---|---|---|
| | 1 | 2 | 3 | 4 | 5 | 6 | 7 |
| Water Phase: | | | | | | | |
| Water | qs | qs | qs | qs | qs | qs | qs |
| Glycerin | 2.0 | 5.0 | 10.0 | 25.5 | — | 2.0 | 5.0 |
| Propylene glycol | — | — | — | — | 3.0 | 2.0 | 1.0 |
| Butylene glycol | — | — | — | — | 3.0 | 2.0 | 2.0 |
| Niacinamide | 2.0 | 5.0 | 1.0 | 2.0 | 2.0 | 4.0 | 4.0 |
| D-panthenol | 0.5 | 2.0 | — | 0.5 | 1.0 | 1.0 | 0.5 |
| Palmitoyl-pentapeptide[1] | 0.0002 | — | — | — | — | — | 0.0003 |
| N-acetyl glucosamine | 2.0 | — | — | — | — | 1.5 | — |
| Green tea extract | 0.5 | — | — | 0.5 | — | — | — |
| Polysorbate 20 | — | — | — | — | 0.2 | 0.4 | — |
| Glycereth-25 PCA isostearate | — | — | 0.2 | — | — | — | — |
| Disodium EDTA | 0.05 | 0.1 | 0.05 | 0.05 | 0.05 | 0.05 | 0.05 |
| Methylparaben | — | — | 0.1 | 0.1 | 0.1 | 0.1 | 0.1 |
| Benzyl alcohol | 0.2 | 0.2 | 0.2 | 0.2 | 0.2 | — | 0.2 |
| Phenoxyethanol | 0.2 | 0.2 | — | — | — | 0.2 | — |
| FD&C Red #40 | 0.0001 | — | — | — | — | — | — |
| EL7040[2] | 5.0 | 10.0 | 10.0 | 5.0 | 5.0 | 10.0 | 5.0 |
| KSG-320[3] | — | — | — | 5.0 | — | 2.0 | — |
| Thickener: | | | | | | | |
| Keltrol CG-SFT[4] | — | — | 0.1 | — | — | — | — |
| Veegum Ultra[5] | — | — | — | — | 0.5 | — | — |
| Methocel 40-101[6] | — | — | — | — | 0.2 | — | — |
| Simulgel INS-100[7] | — | — | — | 0.5 | — | — | — |
| Sepigel 305[8] | — | — | — | 0.5 | — | — | — |
| Makimousse-12[9] | 0.4 | 0.6 | 0.4 | 0.3 | 0.2 | — | — |
| Makimousse-25[10] | — | — | — | — | 0.2 | 0.6 | — |
| Aqua Keep 10SH-NF[11] | — | — | — | — | — | — | 0.8 |
| Total: | 100% | 100% | 100% | 100% | 100% | 100% | 100% |

[1] Palmitoyl-lysine-threonine-threonine-lysine-serine, from Sederma
[2] Caprylyl methicone and PEG-12 dimethicone/PPG-20 crosspolymer, from Dow Corning
[3] PEG-15/lauryl dimethicone crosspolymer and isododecane, from Shinetsu
[4] Xanthan gum, from CP Kelco
[5] Magnesium aluminum silicate, from RT Vanderbilt Inc.
[6] Hydroxypropyl methylcellulose, from Dow Chemical Co.
[7] Sodium acrylate/sodium acryloyldimethyl taurate copolymer, isohexadecane, and polysorbate 80, from Seppic
[8] Polyacrylamide, C13-14 isoparaffin, and laureth-7, from Seppic
[9] Sodium polyacrylate starch, from Kobo Products Inc.
[10] Sodium polyacrylate starch, from Kobo Products Inc.
[11] Sodium polyacrylate, from Kobo Products Inc.

Emulsion Compositions

The following are examples of emulsion compositions that utilize combinations of the superabsorbent polymer and silicone elastomer.

The compositions in examples 8 to 14 are prepared as follows. In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a rotor-stator mill). The thickener is then added to the emulsion and the emulsion is cooled to 45° C. while stirring. At 45° C., the remaining additional ingredients are added. The product is then cooled with stirring to 30° C., milled again, and then poured into suitable containers.

|  | Example | | | | | | |
|---|---|---|---|---|---|---|---|
|  | 8 | 9 | 10 | 11 | 12 | 13 | 14 |
| Water Phase: | | | | | | | |
| Water | qs | qs | qs | qs | qs | qs | qs |
| Glycerin | 3.0 | 5.0 | 7.0 | — | 10.0 | 10.0 | 15.0 |
| Propylene glycol | 3.0 | 1.0 | — | 3.0 | 2.0 | — | — |
| Butylene glycol | — | 1.0 | — | 3.0 | — | — | 1.0 |
| Disodium EDTA | 0.05 | 0.1 | 0.05 | 0.1 | 0.1 | 0.05 | 0.1 |
| Methylparaben | 0.1 | 0.1 | 0.1 | 0.1 | 0.1 | 0.1 | 0.1 |
| Niacinamide | 2.0 | 0.5 | — | 3.0 | 5.0 | 3.0 | 5.0 |
| D-panthenol | 0.5 | 0.1 | 1.0 | 0.5 | 0.5 | 0.5 | 1.5 |
| Benzyl alcohol | 0.25 | 0.25 | 0.25 | 0.25 | 0.25 | 0.25 | 0.25 |
| FD&C Red #40 | — | — | — | — | — | — | — |
| Hexamidine diisethionate | 0.01 | — | — | — | — | — | — |
| Palmitoyl-pentapeptide[1] | 0.0003 | — | — | — | — | — | 0.0003 |
| N-acetyl glucosamine | 2.0 | — | 2.0 | — | — | — | 5.0 |
| Oil Phase: | | | | | | | |
| Isohexadecane | 3.0 | 3.0 | 2.0 | 4.0 | 3.0 | 3.0 | — |
| Isopropyl isostearate | 1.0 | 3.0 | 2.0 | 4.0 | 2.0 | 1.0 | 4.0 |
| Sucrose polyester | 0.7 | — | 0.7 | 1.0 | 1.0 | 1.0 | 0.7 |
| EL8051-IN[2] | 4.0 | 5.0 | — | 3.0 | 2.0 | — | 2.0 |
| DC9045[3] | — | — | 5.0 | 3.0 | — | — | — |
| Cetyl alcohol | 0.4 | 0.3 | 0.4 | 0.5 | 1.0 | 0.5 | 1.0 |
| Stearyl alcohol | 0.5 | 0.3 | 0.5 | 0.6 | 1.0 | 0.6 | 1.0 |
| Behenyl alcohol | 0.4 | 0.3 | 0.4 | 0.5 | 1.0 | 0.5 | — |
| PEG-100 stearate | 0.2 | 0.1 | 0.1 | 0.2 | 0.2 | 0.3 | 0.1 |
| Stearic acid | 0.1 | 0.05 | — | 0.2 | 0.2 | 0.2 | 0.1 |
| Cetearyl glucoside | 0.1 | 0.2 | 0.4 | 0.2 | 0.2 | 0.1 | 0.2 |
| Thickener: | | | | | | | |
| Keltrol CG-SFT[4] | — | — | 0.1 | — | — | — | — |
| Veegum Ultra[5] | — | — | — | — | 0.5 | — | — |
| Methocel 40-101[6] | — | — | — | — | 0.2 | — | — |
| Simulgel INS-100[7] | — | — | — | 0.5 | — | — | — |
| Sepigel 305[8] | — | — | — | 0.5 | — | — | — |
| Makimousse-12[9] | 0.4 | 0.6 | 0.4 | 0.3 | 0.2 | — | — |
| Makimousse-25[10] | — | — | — | — | 0.2 | 0.6 | — |
| Aqua Keep 10SH-NF[11] | — | — | — | — | — | — | 0.8 |
| Additional Ingredients: | | | | | | | |
| Dimethicone | 2.0 | 1.0 | — | — | — | — | 2.0 |
| Fragrance | — | 0.1 | 0.1 | 0.1 | 0.1 | 0.1 | — |
| EL7040[12] | 5.0 | — | — | — | 5.0 | 10.0 | 5.0 |
| Polymethylsilsequioxane | — | — | 0.5 | — | — | — | 2.0 |
| Tapioca Pure[13] | 3.0 | 1.0 | — | 5.0 | — | — | 0.5 |
| DryFlo TS[14] | — | 1.0 | 3.0 | — | — | 5.0 | — |
| Total: | 100% | 100% | 100% | 100% | 100% | 100% | 100% |

[1]Palmitoyl-lysine-threonine-threonine-lysine-serine, from Sederma
[2]Isodecyl neopentanoate and dimethicone/bis isobutyl PPG-20 crosspolymer, from Dow Corning
[3]Cyclopentasiloxane and dimethicone crosspolymer, from Dow Corning
[4]Xanthan gum, from CP Kelco
[5]Magnesium aluminum silicate, from RT Vanderbilt Inc.
[6]Hydroxypropyl methylcellulose, from Dow Chemical Co.
[7]Sodium acrylate/sodium acryloyldimethyl taurate copolymer, isohexadecane, and polysorbate 80, from Seppic
[8]Polyacrylamide, C13-14 isoparaffin, and laureth-7, from Seppic
[9]Sodium polyacrylate starch, from Kobo Products Inc.
[10]Sodium polyacrylate starch, from Kobo Products Inc.
[11]Sodium polyacrylate, from Kobo Products Inc.
[12]Caprylyl methicone and PEG-12 dimethicone/PPG-20 crosspolymer
[13]Tapioca powder, from Akzo Nobel
[14]Tapioca and polymethylsilsesquioxane, from Akzo Nobel The compositions in examples 15 to 21 are prepared as follows. In a suitable vessel, the water phase ingredients are combined and stirred until uniform, warming slightly if necessary. In a separate suitable vessel, the oil phase ingredients are combined and mixed until uniform. Next the oil phase is added to the water phase and the resulting emulsion is milled (e.g., with a rotor-stator mill) The thickener is then added to the emulsion and the emulsion is stirred until uniform. The remaining ingredients are then added, the batch is stirred until uniform, the batch is milled again, and the batch is then poured into suitable containers.

Sunscreen Compositions

The following are examples of sunscreen compositions that utilize combinations of superabsorbent polymers and silicone elastomers. The compositions in examples 22 to 27 are prepared as follows. In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a rotor-stator mill). The thickener is then added to the emulsion and the emulsion is cooled to 45° C. while stirring. At

|  | 15 | 16 | 17 | 18 | 19 | 20 | 21 |
|---|---|---|---|---|---|---|---|
| Water Phase: | | | | | | | |
| Water | qs | qs | qs | qs | qs | qs | qs |
| Glycerin | 3.0 | 5.0 | 7.0 | 10.0 | 15.0 | 5.0 | 15.0 |
| Propylene glycol | 3.0 | 1.0 | — | 3.0 | 2.0 | — | — |
| Butylene glycol | — | 1.0 | — | 3.0 | — | — | 1.0 |
| Disodium EDTA | 0.1 | 0.1 | 0.05 | 0.1 | 0.05 | 0.05 | 0.1 |
| Niacinamide | 2.0 | 0.5 | — | 3.0 | 5.0 | 3.0 | 5.0 |
| D-panthenol | 0.5 | 0.1 | 1.0 | 0.5 | 0.5 | 0.5 | 1.5 |
| FD&C Red #40 | — | — | 0.0002 | — | — | — | — |
| FD&C Yellow #10 | — | — | — | — | — | — | 0.0004 |
| Palmitoyl-pentapeptide[1] | 0.0003 | — | — | — | — | — | 0.0003 |
| N-acetyl glucosamine | 2.0 | — | 2.0 | — | — | — | 5.0 |
| Polysorbate 20 | 0.5 | 0.5 | 0.5 | 0.5 | 0.5 | 0.5 | 0.5 |
| Laureth-4 | 0.1 | 0.2 | 0.3 | 0.1 | 0.1 | 0.1 | 0 |
| Silicone/Oil Phase: | | | | | | | |
| Cyclomethicone D5 | 10.0 | 5.0 | 8.0 | 10.0 | 10.0 | — | 10.0 |
| DC 9040[2] | — | 10.0 | 5.0 | — | 5.0 | — | — |
| DC 9041[3] | — | — | — | — | — | 10.0 | — |
| KSG-15[4] | 5.0 | — | — | — | — | — | — |
| Velvesil125[5] | — | — | 5.0 | — | — | — | — |
| EL8051 IN[6] | — | — | — | 10.0 | 5.0 | — | 5.0 |
| DC1503[7] | — | 1.0 | 1.0 | — | — | — | — |
| Dimethicone 5 csk | — | — | — | — | — | 10.0 | — |
| Dimethicone 50 csk | 3.0 | — | — | — | 2.0 | — | — |
| Vitamin E Acetate | — | 0.5 | — | 0.1 | — | — | 0.1 |
| Thickener: | | | | | | | |
| Keltrol CG-SFT[8] | — | — | 0.1 | — | — | — | — |
| Veegum Ultra[9] | — | — | — | — | 0.5 | — | — |
| Methocel 40-101[10] | — | — | — | — | — | 0.2 | — |
| Simulgel INS-100[11] | — | — | — | 0.5 | — | — | — |
| Sepigel 305[12] | — | — | — | 0.5 | — | — | — |
| Makimousse-12[13] | 0.4 | 0.6 | 0.4 | 0.3 | 0.2 | — | — |
| Makimousse-25[14] | — | — | — | — | 0.2 | 0.6 | — |
| Aqua Keep 10SH-NF[15] | — | — | — | — | — | — | 0.8 |
| Additional Ingredients: | | | | | | | |
| Fragrance | — | 0.1 | 0.1 | 0.1 | 0.1 | 0.1 | — |
| EL7040[16] | 5.0 | 5.0 | — | — | — | — | — |
| Tapioca Pure[17] | 1.0 | 1.0 | — | 2.0 | — | — | 0.5 |
| DryFlo TS[18] | — | 1.0 | 1.0 | — | — | 2.0 | — |
| Total: | 100% | 100% | 100% | 100% | 100% | 100% | 100% |

[1]Palmitoyl-lysine-threonine-threonine-lysine-serine available from Sederma (France)
[2]Cyclopentasiloxane and dimethicone crosspolymer, from Dow Corning
[3]Dimethicone and dimethicone crosspolymer, from Dow Corning
[4]Cyclopentasiloxane and dimethicone/vinyl dimethicone crosspolymer, from Shin Etsu
[5]Cyclopentasiloxane and C30-45 alkyl cetearyl dimethicone crosspolymer, from Momentive
[6]Isodecyl neopentanoate and dimethicone/bis isobutyl PPG-20 crosspolymer, from Dow Corning
[7]Dimethicone and dimethiconol, from Dow Corning
[8]Xanthan gum, from CP Kelco
[9]Magnesium aluminum silicate, from RT Vanderbilt Inc.
[10]Hydroxypropyl methylcellulose, from Dow Chemical Co.
[11]Sodium acrylate/sodium acryloyldimethyl taurate copolymer, isohexadecane, and polysorbate 80, from Seppic
[12]Polyacrylamide, C13-14 isoparaffin, and laureth-7, from Seppic
[13]Sodium polyacrylate starch, from Kobo Products Inc.
[14]Sodium polyacrylate starch, from Kobo Products Inc.
[15]Sodium polyacrylate, from Kobo Products Inc.
[16]Caprylyl methicone and PEG-12 dimethicone/PPG-20 crosspolymer
[17]Tapioca powder, from Akzo Nobel
[18]Tapioca and polymethylsilsesquioxane, from Akzo Nobel 45° C., the remaining additional ingredients are added. The product is then cooled with stirring to 30° C., milled again, and then poured into suitable containers.

|  | 22 | 23 | 24 | 25 | 26 | 27 |
|---|---|---|---|---|---|---|
| Water Phase: | | | | | | |
| Water | qs | qs | qs | qs | qs | qs |
| Glycerin | 3.0 | 5.0 | 7.0 | 10.0 | 15.0 | 5.0 |
| Disodium EDTA | 0.1 | 0.1 | 0.05 | 0.1 | 0.05 | 0.05 |
| Methylparaben | 0.2 | 0.2 | 0.2 | 0.2 | 0.2 | 0.2 |
| Niacinamide | 2.0 | 0.5 | — | 3.0 | 5.0 | 3.0 |
| D-panthenol | 0.5 | 0.1 | 1.0 | 0.5 | 0.5 | 0.5 |
| Phenylbenzimidazole Sulfonic Acid | 1.0 | — | — | 0.5 | — | — |
| Triethanolamine | 0.64 | — | — | 0.32 | — | — |
| Benzyl alcohol | 0.25 | 0.25 | 0.25 | 0.25 | 0.25 | 0.25 |
| Oil Phase: | | | | | | |
| Isopropyl Isostearate | 2.0 | 2.0 | 2.0 | 1.0 | — | — |
| Isopropyl lauroylsarcosinate | — | 4.0 | 2.0 | 7.0 | — | 6.0 |
| EL8051 IN[1] | 4.0 | — | — | 5.0 | 5.0 | 10.0 |
| Octisalate | 4.0 | 4.0 | 4.0 | — | — | 4.0 |
| Homosalate | — | 8.0 | — | — | — | — |
| Octocrylene | 1.0 | 2.0 | — | — | 2.0 | 2.0 |
| Octinoxate | — | — | 6.0 | 5.0 | 7.5 | — |
| Tinosorb S[2] | — | — | — | 3.0 | — | 2.0 |
| Oxybenzone | — | 4.0 | — | — | — | — |
| Avobenzone | 2.0 | 3.0 | 2.0 | — | — | 2.0 |
| Solastay S1[3] | — | — | 2.0 | — | — | 2.0 |
| Vitamin E Acetate | 0.5 | 0.1 | 0.5 | 0.1 | 0.1 | 0.1 |
| Ethylparaben | 0.2 | 0.2 | 0.2 | 0.2 | 0.2 | 0.2 |
| Propylparaben | 0.2 | 0.2 | 0.2 | 0.2 | 0.2 | 0.2 |
| Cetyl alcohol | 1.0 | 0.3 | 1.0 | 0.6 | 0.6 | 1.0 |
| Stearyl alcohol | 1.0 | 0.4 | 1.0 | 0.8 | 0.8 | 1.0 |
| Behenyl alcohol | 1.0 | 0.4 | 1.0 | 0.8 | 0.8 | 1.0 |
| Cetearyl Glucoside | 0.3 | 0.3 | 0.3 | 0.3 | 0.3 | 0.3 |
| PEG-100 stearate | 0.3 | 0.3 | 0.3 | 0.3 | 0.3 | 0.3 |
| Thickener: | | | | | | |
| Keltrol CG-SFT[4] | — | — | 0.1 | — | — | — |
| Veegum Ultra[5] | — | — | — | — | 0.5 | — |
| Methocel 40-101[6] | — | — | — | — | 0.2 | — |
| Simulgel INS-100[7] | — | — | — | 0.5 | — | — |
| Sepigel 305[8] | — | — | — | 0.5 | — | — |
| Makimousse-12[9] | 0.4 | 0.6 | 0.4 | 0.3 | 0.2 | — |
| Makimousse-25[10] | — | — | — | — | 0.2 | 0.6 |
| Aqua Keep 10SH-NF[11] | — | — | — | — | — | — |
| Additional Ingredients: | | | | | | |
| Fragrance | — | 0.1 | 0.1 | 0.1 | 0.1 | — |
| EL7040[12] | — | 10.0 | 5.0 | — | — | — |
| Tapioca Pure[13] | 1.0 | 1.0 | — | 2.0 | — | — |
| DryFlo TS[14] | 2.0 | — | 5.0 | — | — | — |
| Tinosorb M[15] | — | — | — | 4.0 | 8.0 | 4.0 |
| DC 1503[16] | 2.0 | 1.0 | — | — | — | — |
| Total: | 100% | 100% | 100% | 100% | 100% | 100% |

[1]Isodecyl neopentanoate and dimethicone/bis isobutyl PPG-20 crosspolymer, from Dow Corning
[2]Bemotrizinol, from BASF
[3]Ethylhexyl Methoxycrylene, from Hallstar
[4]Xanthan gum, from CP Kelco
[5]Magnesium aluminum silicate, from RT Vanderbilt Inc.
[6]Hydroxypropyl methylcellulose, from Dow Chemical Co.
[7]Sodium acrylate/sodium acryloyldimethyl taurate copolymer, isohexadecane, and polysorbate 80, from Seppic
[8]Polyacrylamide, C13-14 isoparaffin, and laureth-7, from Seppic
[9]Sodium polyacrylate starch, from Kobo Products Inc.
[10]Sodium polyacrylate starch, from Kobo Products Inc.
[11]Sodium polyacrylate, from Kobo Products Inc.
[12]Caprylyl methicone and PEG-12 dimethicone/PPG-20 crosspolymer
[13]Tapioca powder, from Akzo Nobel
[14]Tapioca and polymethylsilsesquioxane, from Akzo Nobel
[15]Bisoctrizole, decyl glucoside, xanthan gum, propylene glycol, and water, from BASF
[16]Dimethicone and dimethiconol, from Dow Corning Examples Showing Benefits of Superabsorbent Polymer and Elastomer Combinations The benefits of the combination of the present invention include improved skin appearance and improved product stability. Both benefits, as evidenced by the data provided below, are unexpected, surprising and synergistic in view of the individual components.

The improved skin appearance of the product is evidenced by measuring the "shine". Specifically, it is known that reducing shine on the skin optically reduces the appearance of fine lines and wrinkles To predict the impact of a product on the shine of the skin, in vitro shine testing is often used. For this in vitro shine testing, a thin film of product is cast on a substrate using a draw down bar applicator (BYK Gardner) or similar device, the product film is allowed to dry, and then the shine of the resulting dry product film is measured using an instrument called a glossmeter (BYK Gardner).

To test out the impact of shine of the present invention, the following four compositions were made as follows. In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a rotor-stator mill) The thickener is then added to the emulsion and the emulsion is cooled while stirring. Separately, the elastomer phase ingredients are combined and mixed until uniform. When the emulsion cools to 55° C., the elastomer phase and remaining additional ingredients are added. The product is then cooled with stirring to 30° C., milled again, and then poured into suitable containers.

|  | 28 | 29 | 30 | 31 |
|---|---|---|---|---|
| Water Phase: | | | | |
| Water | qs | qs | qs | qs |
| Disodium EDTA | 0.05 | 0.05 | 0.05 | 0.05 |
| Methylparaben | 0.25 | 0.25 | 0.25 | 0.25 |
| Niacinamide | 2.0 | 2.0 | 2.0 | 2.0 |
| D-panthenol | 0.5 | 0.5 | 0.5 | 0.5 |
| Benzyl alcohol | 0.5 | 0.5 | 0.5 | 0.5 |
| Oil Phase: | | | | |
| Octisalate | 1.235 | 1.235 | 1.235 | 1.235 |
| Homosalate | 2.475 | 2.475 | 2.475 | 2.475 |
| Octocrylene | 0.715 | 0.715 | 0.715 | 0.715 |
| Avobenzone | 0.825 | 0.825 | 0.825 | 0.825 |
| Ethylparaben | 0.2 | 0.2 | 0.2 | 0.2 |
| Propylparaben | 0.15 | 0.15 | 0.15 | 0.15 |
| Cetyl alcohol | 0.3 | 0.3 | 0.3 | 0.3 |
| Stearyl alcohol | 0.4 | 0.4 | 0.4 | 0.4 |
| Behenyl alcohol | 0.4 | 0.4 | 0.4 | 0.4 |
| Emulgade PL68/50[1] | 0.2 | 0.2 | 0.2 | 0.2 |
| PEG-100 stearate | 0.2 | 0.2 | 0.2 | 0.2 |
| Stearic acid | 0.05 | 0.05 | 0.05 | 0.05 |
| Elastomer Phase: | | | | |
| Cyclopentasiloxane | — | — | 2.0 | 2.0 |
| EL8050 ID[2] | — | — | 5.0 | 5.0 |
| Polysorbate 20 | — | — | 0.2 | 0.2 |
| Thickener: | | | | |
| Keltrol CG-SFT[3] | — | 0.1 | — | 0.1 |
| Simulgel INS-100[4] | 1.8 | — | 1.8 | — |
| Makimousse-12[5] | — | 0.4 | — | 0.4 |
| Additional Ingredients: | | | | |
| Microthene FN510[6] | 0.5 | 0.5 | 0.5 | 0.5 |
| Ropearl 4000[7] | 0.75 | 0.75 | 0.75 | 0.75 |

-continued

|  | 28 | 29 | 30 | 31 |
|---|---|---|---|---|
| DC 1503[8] | 2.0 | 2.0 | 2.0 | 2.0 |
| Glycacil L[9] | 0.09 | 0.09 | 0.09 | 0.09 |
| Total: | 100% | 100% | 100% | 100% |

[1]Cetearyl glucoside and cetearyl alcohol, from Cognis
[2]Isododecane and dimethicone/bis isobutyl PPG-20 crosspolymer, from Dow Corning
[3]Xanthan gum, from CP Kelco
[4]Sodium acrylate/sodium acryloyldimethyl taurate copolymer, isohexadecane, and polysorbate 80, from Seppic
[5]Sodium polyacrylate starch, from Kobo Products Inc.
[6]Polyethylene homopolymer, from Equistar
[7]Nylon-12, from Kobo Products Inc.
[8]Dimethicone and dimethiconol, from Dow Corning
[9]Iodopropynyl butylcarbamate, from Lonza Next, these four formulations were subjected to in vitro shine testing as described above. As can be seen from the results of this testing provided below, both the superabsorbent polymer and elastomers reduce shine individually when added to the base formulation (example 28). Importantly, the combination of these two materials leads to much lower levels of shine than achieved with either alone. Hence, this combination of materials would be expected to provide significant skin appearance benefits.

| Example | Formula Description | Shine (85°) |
|---|---|---|
| 28 | Base emulsion | 78.6 |
| 29 | Base emulsion with superabsorbent polymer | 34.4 |
| 30 | Base emulsion with elastomer | 11.6 |
| 31 | Base emulsion with superabsorbent polymer and elastomer | 4.2 |

Additionally, shelf stability testing of a similar set of formulations shows the stability benefits for the combination of superabsorbent polymer plus elastomer. Generally stable formulations will show either no change or an increase in viscosity upon aging (the viscosity growth is typical of strengthening gel network structure during aging). For stability testing, the following products below were made as follows. In a suitable vessel, the water phase ingredients are combined and heated to 75° C. In a separate suitable vessel, the oil phase ingredients are combined and heated to 75° C. Next the oil phase is added to the water phase and the resulting emulsion is milled (e.g., with a rotor-stator mill). The thickener is then added to the emulsion and the emulsion is cooled while stirring. Separately, the elastomer phase ingredients are combined and mixed until uniform. When the emulsion cools to 55° C., the elastomer phase and remaining additional ingredients are added. The product is then cooled with stirring to 30° C., milled again, and then poured into suitable containers.

|  | 32 | 33 | 34 | 35 | 36 | 37 | 38 | 39 | 40 | 41 |
|---|---|---|---|---|---|---|---|---|---|---|
| Water Phase: |  |  |  |  |  |  |  |  |  |  |
| Water | qs | qs | qs | qs | qs | qs | qs | qs | qs | qs |
| Disodium EDTA | 0.05 | 0.05 | 0.05 | 0.05 | 0.05 | 0.05 | 0.05 | 0.05 | 0.05 | 0.05 |
| Methylparaben | 0.25 | 0.25 | 0.25 | 0.25 | 0.25 | 0.25 | 0.25 | 0.25 | 0.25 | 0.25 |
| Niacinamide | 2.0 | 2.0 | 2.0 | 2.0 | 2.0 | 2.0 | 2.0 | 2.0 | 2.0 | 2.0 |
| D-panthenol | 0.5 | 0.5 | 0.5 | 0.5 | 0.5 | 0.5 | 0.5 | 0.5 | 0.5 | 0.5 |
| Benzyl alcohol | 0.5 | 0.5 | 0.5 | 0.5 | 0.5 | 0.5 | 0.5 | 0.5 | 0.5 | 0.5 |
| Oil Phase: |  |  |  |  |  |  |  |  |  |  |
| Isopropyl isostearate | — | — | 1.33 | — | — | — | — | — | — | — |
| Octisalate | 2.47 | 1.235 | 2.47 | 2.47 | 1.235 | 1.235 | 1.235 | 1.235 | 2.47 | 2.47 |
| Homosalate | 4.95 | 2.475 | 4.95 | 4.95 | 2.475 | 2.475 | 2.475 | 2.475 | 4.95 | 4.95 |
| Octocrylene | 1.43 | 0.715 | 1.43 | 1.43 | 0.715 | 0.715 | 0.715 | 0.715 | 1.43 | 1.43 |
| Oxybenzone | — | — | — | — | — | — | — | — | — | — |
| Avobenzone | 1.65 | 0.825 | 1.65 | 1.65 | 0.825 | 0.825 | 0.825 | 0.825 | 1.65 | 1.65 |
| Ethylparaben | 0.2 | 0.2 | 0.2 | 0.2 | 0.2 | 0.2 | 0.2 | 0.2 | 0.2 | 0.2 |
| Propylparaben | 0.15 | 0.15 | 0.15 | 0.15 | 0.15 | 0.15 | 0.15 | 0.15 | 0.15 | 0.15 |
| Cetyl alcohol | 0.3 | 0.3 | 0.3 | 0.3 | 0.3 | 0.3 | 0.3 | 0.3 | 0.3 | 0.3 |
| Stearyl alcohol | 0.4 | 0.4 | 0.4 | 0.4 | 0.4 | 0.4 | 0.4 | 0.4 | 0.4 | 0.4 |
| Behenyl alcohol | 0.4 | 0.4 | 0.4 | 0.4 | 0.4 | 0.4 | 0.4 | 0.4 | 0.4 | 0.4 |
| Emulgade PL68/50[1] | 0.2 | 0.2 | 0.2 | 0.2 | 0.2 | 0.2 | 0.2 | 0.2 | 0.2 | 0.2 |
| PEG-100 stearate | 0.2 | 0.2 | 0.2 | 0.2 | 0.2 | 0.2 | 0.2 | 0.2 | 0.2 | 0.2 |
| Stearic acid | 0.05 | 0.05 | 0.05 | 0.05 | 0.05 | 0.05 | 0.05 | 0.05 | 0.05 | 0.05 |
| Elastomer Phase: |  |  |  |  |  |  |  |  |  |  |
| Cyclopentasiloxane | — | — | — | — | — | 9.0 | 2.0 | 2.0 | 9.0 | 2.5 |
| EL8050 ID[2] | — | — | — | — | — | 9.0 | 5.0 | 5.0 | 9.0 | 10.0 |
| Polysorbate 20 | — | — | — | — | — | 0.2 | 0.2 | 0.2 | 0.2 | 0.2 |
| Thickener: |  |  |  |  |  |  |  |  |  |  |
| Keltrol CG-SFT[3] | — | — | 0.1 | — | — | — | — | 0.1 | 0.1 | 0.1 |
| Simulgel INS-100[4] | 1.8 | 1.8 | — | — | — | 0.8 | 1.8 | — | — | — |
| Makimousse-12[5] | — | — | 0.4 | 0.6 | 0.6 | — | — | 0.4 | 0.4 | 0.4 |
| Additional Ingredients: |  |  |  |  |  |  |  |  |  |  |
| Microthene FN510[6] | 1.0 | 0.5 | 1.0 | 1.0 | 0.5 | 0.5 | 0.5 | 0.5 | 1.0 | 1.0 |
| Ropearl 4000[7] | 1.5 | 0.75 | 1.5 | 1.5 | 0.75 | 0.75 | 0.75 | 0.75 | 1.5 | 1.5 |

-continued

|  | 32 | 33 | 34 | 35 | 36 | 37 | 38 | 39 | 40 | 41 |
|---|---|---|---|---|---|---|---|---|---|---|
| DC 1503[8] | 2.0 | 2.0 | 2.0 | 2.0 | 2.0 | 1.0 | 2.0 | 2.0 | 1.0 | 2.0 |
| Glycacil L[9] | 0.09 | 0.09 | 0.09 | 0.09 | 0.09 | 0.09 | 0.09 | 0.09 | 0.09 | 0.09 |
| Total: | 100% | 100% | 100% | 100% | 100% | 100% | 100% | 100% | 100% | 100% |

[1] Cetearyl glucoside and cetearyl alcohol, from Cognis
[2] Isododecane and dimethicone/bis isobutyl PPG-20 crosspolymer, from Dow Corning
[3] Xanthan gum, from CP Kelco
[4] Sodium acrylate/sodium acryloyldimethyl taurate copolymer, isohexadecane, and polysorbate 80, from Seppic
[5] Sodium polyacrylate starch, from Kobo Products Inc.
[6] Polyethylene homopolymer, from Equistar
[7] Nylon-12, from Kobo Products Inc.
[8] Dimethicone and dimethiconol, from Dow Corning
[9] Iodopropynyl butylcarbamate, from Lonza As shown below, while the base emulsion with a conventional thickener (Simulgel INS-100) and the base emulsion with a superabsorbent polymer thickener both showed acceptable stability after 5 months of aging under room temperature conditions, the emulsions containing both the conventional thickener (Simulgel INS-100) and elastomer showed a significant loss of viscosity upon aging. In contrast, the superabsorbent polymer plus elastomer systems did not show any significant loss in viscosity when subjected to similar aging conditions.

| Example | Description | Initial Viscosity (cps) | Aged Viscosity (cps) | Viscosity Change (cps) |
|---|---|---|---|---|
| 32 | Base emulsion | 46,600 | 63,000 | +18,400 |
| 33 | Base emulsion | 49,000 | 61,000 | +12,000 |
| 34 | Base emulsion with superabsorbent polymer | 58,600 | 67,000 | +8,400 |
| 35 | Base emulsion with superabsorbent polymer | 73,200 | 90,400 | +17,200 |
| 36 | Base emulsion with superabsorbent polymer | 82,600 | 91,400 | +8,800 |
| 37 | Base emulsion with elastomer | 47,400 | 41,400 | −6,000 |
| 38 | Base emulsion with elastomer | 38,400 | 28,000 | −10,400 |
| 39 | Base emulsion with superabsorbent polymer and elastomer | 50,600 | 49,000 | −1,600 |
| 40 | Base emulsion with superabsorbent polymer and elastomer | 38,000 | 41,800 | +3,800 |
| 41 | Base emulsion with superabsorbent polymer and elastomer | 42,000 | 46,600 | +4,600 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A thickened aqueous composition comprising:
   a. from about 0.01% to about 10%, by weight, of a superabsorbent polymer in the form of sodium polyacrylate starch particles having a non-swollen, number-average particle size of between 2 and 100 microns;
   b. from about 0.1% to about 20%, by weight, of a silicone elastomer; and
   c. from about 20% to about 98% of water, wherein the superabsorbent polymer is present in the water.

2. The thickened aqueous composition of claim 1 wherein the aqueous composition is mixed with an oil phase to form an oil- in-water or water-in-oil-in-water emulsion.

3. The thickened aqueous composition of claim 2, wherein the aqueous composition further comprises from about 0.01 to about 10%, by weight, of an emulsifier.

4. The thickened aqueous composition of claim 3, wherein the emulsifier is selected from a group consisting of ethers of glycerol, polyglycerol, sucrose, glucose, or sorbitol; esters of glycerol, polyglycerol, sucrose, glucose, or sorbitol; and mixtures thereof.

5. The thickened aqueous composition of claim 1 further comprising from about 1% to about 40%, by weight, of a UV active selected from a group consisting of avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis30 benzotriazolyl tetramethylbutylphenol, and bis-ethylhexyloxyphenol methoxyphenyltriazine, 4-methylbenzylidenecamphor, isopentyl 4-methoxycinnamate and combinations thereof.

6. The thickened aqueous composition of claim 5, wherein the UV active is selected from a group consisting of avobenzone, homosalate, octyl salicylate, oxybenzone, phenylbenzimidazole sulfonic acid, titanium dioxide, zinc oxide, ethylhexyl triazone, dioctyl butamido triazone, benzylidene malonate polysiloxane, terephthalylidene 5 dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, isopentyl 4- methoxycinnamate and combinations thereof.

7. The thickened aqueous composition of claim 2, further comprising a solvent is selected from a group consisting of di-isopropyl adipate, butyl phthalimide, isopropyl phthalimide, phenylethyl benzoate, dicaprylyl carbonate, isopropyl lauroylsarcosinate, isononyl isononanoate, butyl octylsalicylate, dioctyl malate, dicaprylyl maleate, isopropyl isostearate, propylene glycol dicaprate, esters of C12-C15 alcohol benzoates, isosorbide diesters, and derivatives and mixtures thereof.

8. The thickened aqueous composition of claim 6 further comprising a photostabilizer.

9. The thickened aqueous composition of claim 8 wherein the photostabilizer is selected from a group consisting of methoxycrylene, diethylhexyl 2,6-naphthalate, diethylhexyl syringylidenemalonate, and combinations thereof.

10. The thickened aqueous composition of claim 1 further comprising an active or agent selected from a group consisting of sugar amines, vitamins, oil control agents, humectants, emollients, photosterols, hexamidine compounds, tightening agents, anti-wrinkle actives, anti-atrophy actives, flavonoids, N-acyl amino acid compounds, retinoids, peptides, particulate materials, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, substantivity polymers, detersive surfactants, and combinations thereof.

11. The thickened aqueous composition of claim 10 wherein the vitamins are selected from vitamin B3 compound, ascorbic acid, tocopherol acetate, panthenol, dexpanthenol, magnesium ascorbyl phosphate, sodium ascorbyl phosphate, retinyl propionate, and combinations thereof.

12. The thickened aqueous composition of claim 10 wherein the active or agent is selected from glucosamine, glucosamine derivatives, salts of dehydroacetic acid, salicylic acid, hexamidine diisethionate, salts of dialkanoyl hydroxyproline, N-acyl phenylalanine, dipeptides, 10 pentapeptides, titanium dioxide, iron oxide, zinc oxide, butylated hydroxytoluene, dihydroxyacetone, and combinations thereof.

13. The thickened aqueous composition of claim 2 wherein the oil phase is from about 1% to about 60%, by weight, of the emulsion.

14. The thickened aqueous composition of claim 6 wherein one or more of the UV actives is encapsulated.

15. The thickened aqueous composition of claim 1 further comprising from about 0.01% to about 10%, by weight, of a gum, clay, cellulose, modified cellulosic composition, and mixtures thereof.

16. The thickened aqueous composition of claim 1 wherein the silicone elastomer is a nonemulsifying elastomer.

17. The thickened aqueous composition of claim 16 wherein the non-emulsifying elastomer is selected from the group consisting of dimethicone crosspolymers, dimethicone/vinyl dimethicone crosspolymers, copolymers, and their derivatives, C30-45 alkyl cetearyl dimethicone crosspolymer, cetearyl dimethicone crosspolymer, copolymers, and their derivatives, dimethicone/phenyl vinyl dimethicone crosspolymer, vinyl dimethicone/lauryl dimethicone crosspolymer, copolymers, and their derivatives and mixtures thereof.

18. The thickened aqueous composition of claim 1 wherein the silicone elastomer is an emulsifying elastomer.

19. The thickened aqueous composition of claim 18 wherein the emulsifying elastomer is selected from the group consisting of polyoxyethylene silicone elastomer, polyglycerin-modified silicone elastomers, alkyl-containing polyoxyethylene silicone elastomers, alkyl containing polyglycerin-modified silicone elastomers, polyoxypropylene silicone elastomers, and mixtures thereof.

* * * * *